(12) United States Patent
Varshavskaya et al.

(10) Patent No.: US 10,072,927 B2
(45) Date of Patent: Sep. 11, 2018

(54) DETECTING A SUBSTRATE

(71) Applicant: RareCyte, Inc., Seattle, WA (US)

(72) Inventors: Paulina Varshavskaya, Seattle, WA (US); Edward Shafer, Bellevue, WA (US); Steve Quarre, Woodinville, WA (US); Ronald C. Seubert, Sammamish, WA (US)

(73) Assignee: RareCyte, Inc., Seattle, WA (US)

( * ) Notice: Subject to any disclaimer, the term of this patent is extended or adjusted under 35 U.S.C. 154(b) by 96 days.

(21) Appl. No.: 14/989,907

(22) Filed: Jan. 7, 2016

(65) Prior Publication Data

US 2017/0199033 A1 Jul. 13, 2017

(51) Int. Cl.
*G01B 21/16* (2006.01)

(52) U.S. Cl.
CPC .................................. *G01B 21/16* (2013.01)

(58) Field of Classification Search
CPC ...................................................... G01B 21/16
See application file for complete search history.

(56) References Cited

U.S. PATENT DOCUMENTS

| | | | |
|---|---|---|---|
| 4,012,112 A | 3/1977 | Masterson | |
| 5,428,997 A | 7/1995 | Paulsen | |
| 5,459,384 A | 10/1995 | Engelse et al. | |
| 5,587,833 A | 12/1996 | Kamentsky | |
| 5,652,377 A | 7/1997 | Yagi | |
| 5,677,635 A | 10/1997 | Fujii et al. | |
| 6,049,421 A | 4/2000 | Raz et al. | |
| 6,073,485 A | 6/2000 | Kitamura | |
| 6,337,478 B1 | 1/2002 | Uehara et al. | |
| 6,407,858 B1 | 6/2002 | Montagu | |
| 6,507,197 B1 | 1/2003 | Itoh et al. | |
| 6,718,821 B1 | 4/2004 | Houston et al. | |
| 6,847,481 B1 | 1/2005 | Ludl et al. | |
| 7,180,662 B2 | 2/2007 | Rondeau et al. | |
| 7,567,885 B2 | 7/2009 | Herchen et al. | |
| 7,627,153 B2 | 12/2009 | Perz et al. | |
| 7,911,670 B2 | 3/2011 | Bec et al. | |
| 9,222,953 B2 * | 12/2015 | Quarre ................. B01L 3/0217 |
| 9,227,188 B2 * | 1/2016 | Quarre ................. B01L 3/0275 |
| 9,519,002 B2 * | 12/2016 | Nordberg .......... G01N 35/1009 |
| 9,810,605 B2 * | 11/2017 | Nordberg ................. G01N 1/14 |
| 2002/0074512 A1 | 6/2002 | Montagu et al. | |
| 2003/0057379 A1 | 3/2003 | Montagu | |
| 2004/0061049 A1 | 4/2004 | Curry et al. | |
| 2004/0126895 A1 | 7/2004 | Overbeck et al. | |
| 2005/0092080 A1 | 5/2005 | Harazin et al. | |
| 2006/0121602 A1 | 6/2006 | Hoshizaki et al. | |
| 2008/0078262 A1 | 4/2008 | Murata et al. | |
| 2009/0076650 A1 * | 3/2009 | Faes ...................... G07F 11/165 700/232 |
| 2011/0261352 A1 | 10/2011 | Ohta et al. | |
| 2012/0125776 A1 | 5/2012 | van der Wal et al. | |
| 2012/0225435 A1 | 9/2012 | Seger et al. | |
| 2012/0231532 A1 | 9/2012 | Duer | |

(Continued)

FOREIGN PATENT DOCUMENTS

| | | | |
|---|---|---|---|
| DE | 19733297 A1 | 2/1999 | |
| WO | WO 2014169012 A1 * | 10/2014 | ......... G01N 35/1009 |

*Primary Examiner* — Laura Menz

(74) *Attorney, Agent, or Firm* — Shay Glenn LLP

(57) ABSTRACT

This disclosure is directed to a system and method for detecting a surface of a substrate within a scanner.

14 Claims, 8 Drawing Sheets

(56) References Cited

U.S. PATENT DOCUMENTS

| | | | |
|---|---|---|---|
| 2014/0308163 A1* | 10/2014 | Nordberg | G01N 35/1009 422/63 |
| 2015/0037803 A1 | 2/2015 | Park et al. | |
| 2015/0182962 A1* | 7/2015 | Quarre | B01L 3/0275 422/525 |
| 2015/0185243 A1* | 7/2015 | Quarre | G01N 35/1009 422/509 |
| 2015/0231635 A1 | 8/2015 | Okano et al. | |
| 2015/0241426 A1* | 8/2015 | Kaldjian | G01N 33/56911 435/7.92 |
| 2015/0247876 A1* | 9/2015 | Quarre | B01L 3/0217 422/63 |
| 2016/0228869 A1* | 8/2016 | Quarre | B01L 3/0275 |
| 2017/0010188 A1* | 1/2017 | Nordberg | G01N 35/1009 |
| 2017/0199033 A1* | 7/2017 | Varshavskaya | G01B 21/16 |
| 2017/0219463 A1* | 8/2017 | Nordberg | G01M 99/008 |

* cited by examiner

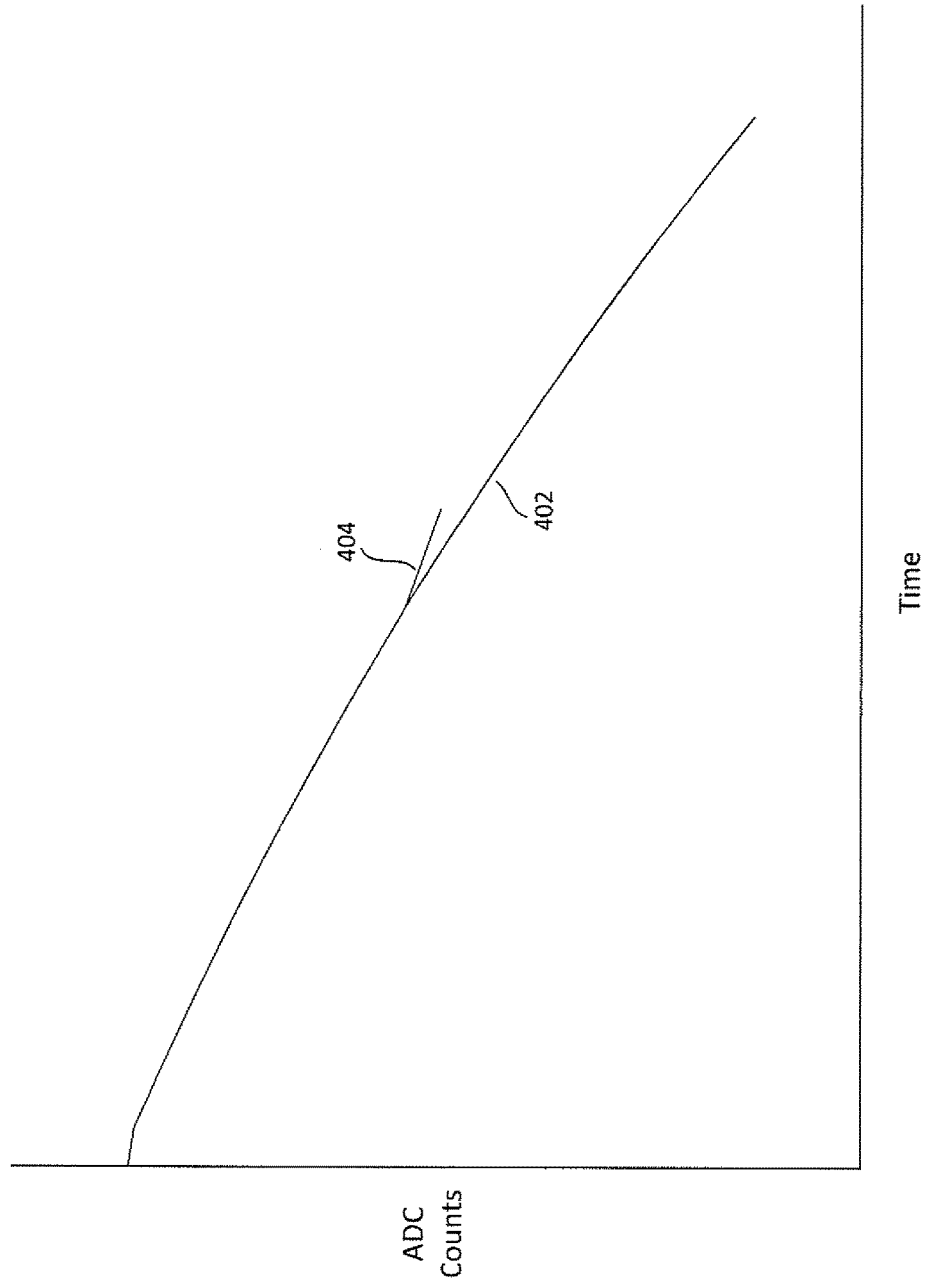

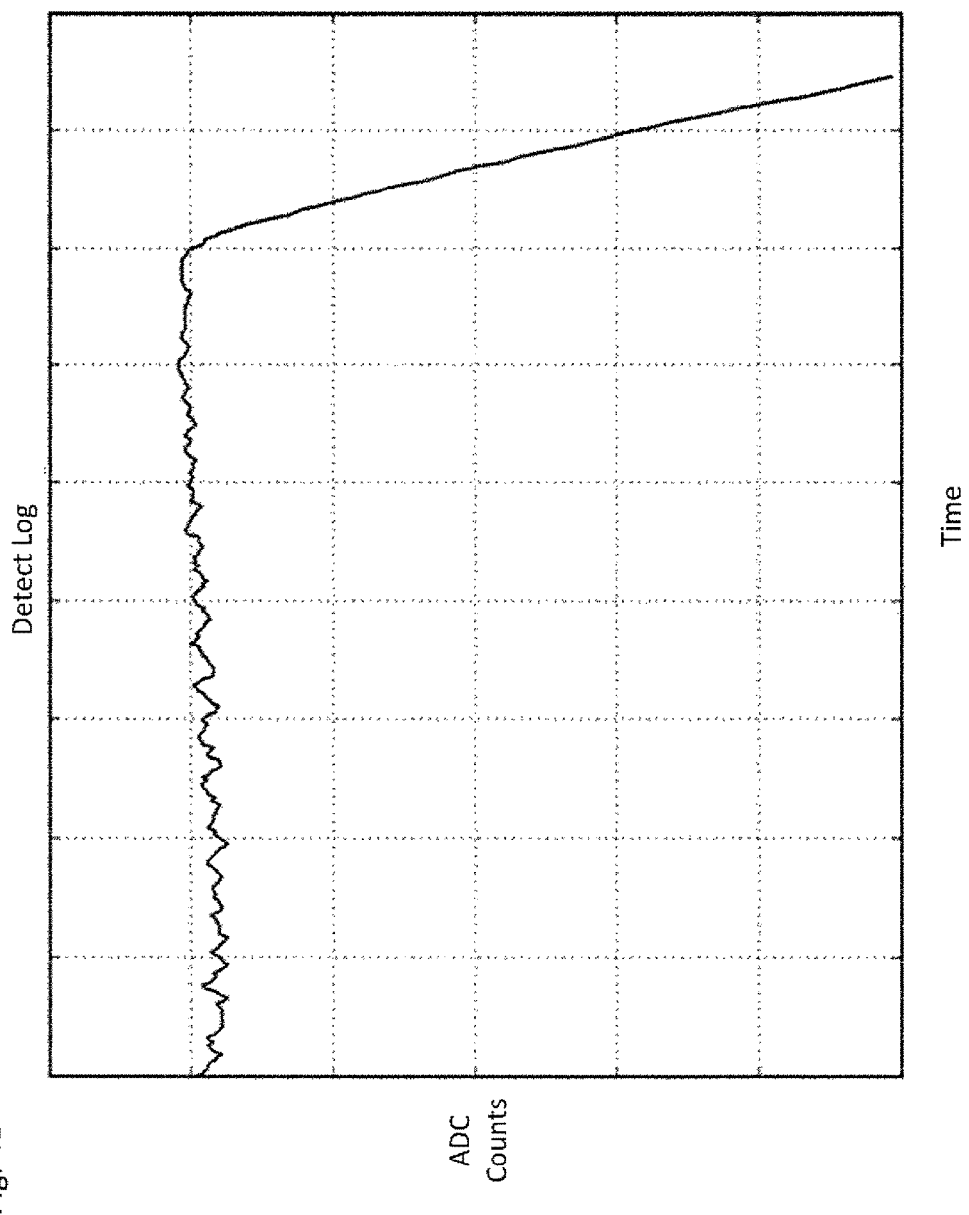

DETECTING A SUBSTRATE

TECHNICAL FIELD

This disclosure relates generally to detecting a substrate, though more specifically, to detecting a slide surface within a scanner.

BACKGROUND

A picker or picking system may be used to isolate a target analyte from a suspension in or on a substrate, such as a well, a well plate, a slide, a tube, or the like, or to draw a fluid, such as a, suspension, solution or reagent, from the substrate. As a result, practitioners, researchers, and those working with suspensions continue to seek systems and methods to more efficiently and accurately detect a substrate surface.

DESCRIPTION OF THE DRAWINGS

FIG. 4A shows a first output and a second output superimposed.
FIG. 4B shows the difference between the first output and the second output of FIG. 4A.

DETAILED DESCRIPTION

This disclosure is directed to a system and method for detecting a surface of a substrate within a scanner.

General Description of a Scanner and Subsystem

Figure 1:
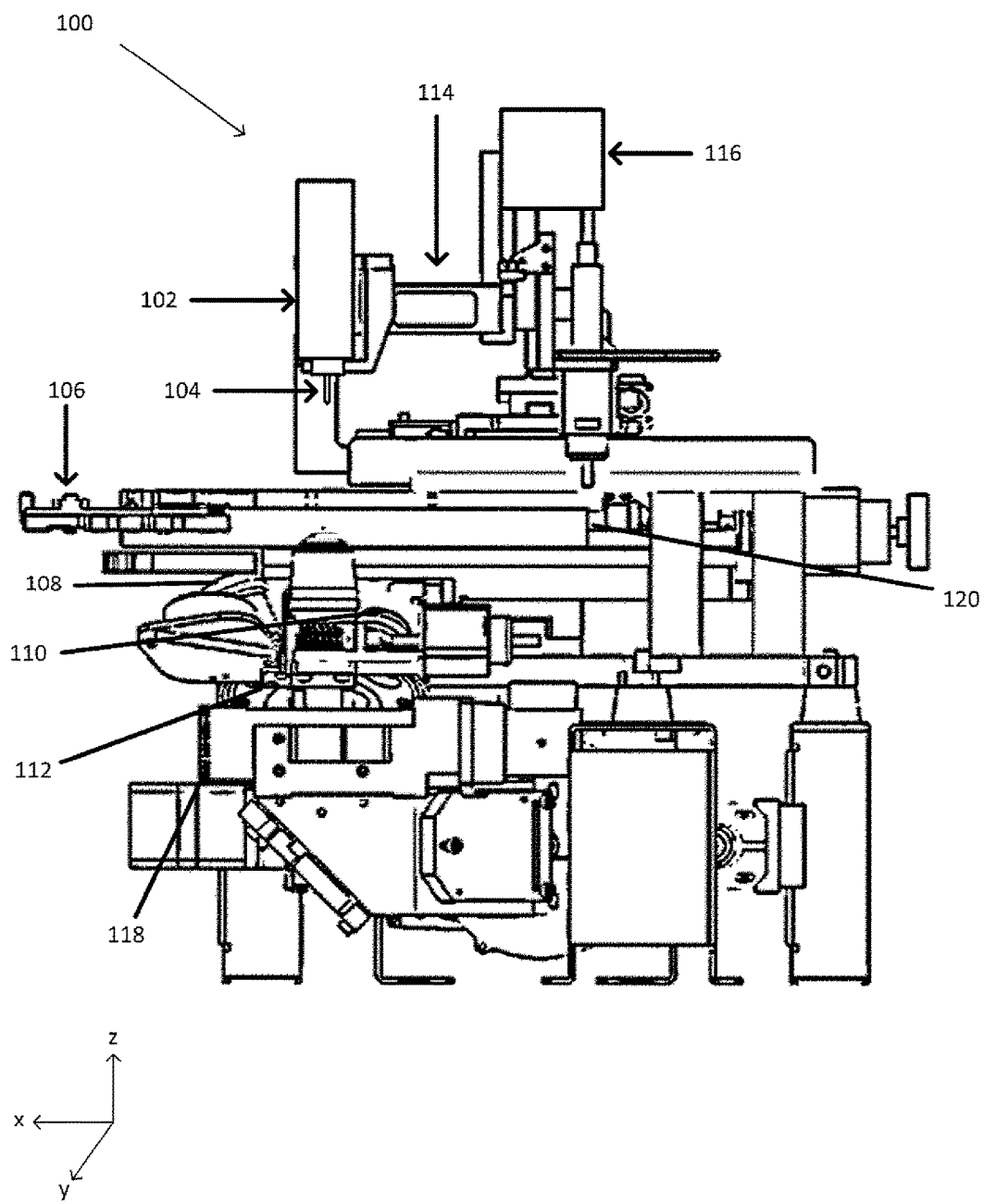
FIG. 1 shows an example scanner.

FIG. 1 shows an isometric view of a scanner 100 with a cover removed. The scanner 100 includes a picker 102 having a picker tip 104. The picker 100 is a device for isolating a target analyte or target material from the remainder of a sample. The picker 102 may be driven along the z-axis by a z-picker motor system, which may include at least one of a coarse z-motor 116 and a fine z-motor 114.

The scanner 100 also includes a slide holder 106 for holding and supporting a substrate (not shown) that includes the sample, such as buffy coat, or a fluid, such as a reagent. The scanner 100 may also include a turret 112, including a first objective 110 and a deflection detector 108, which rotates to bring the first objective 100 and the deflection detector 108 underneath the substrate when it is desirous to do so. The turret 112 may include more than one objective, each objective having different magnification levels, when it is desirous to do so. The deflection detector 108 may be tactile (i.e. touch or pressure sensor), capacitive, optical, acoustic (i.e. sound) or the like. A z-axis turret motor 118 drives the turret 112 along the z-axis, such as towards and away from the substrate or slide holder 106.

A slide motor 120 may be activated to move the slide holder 106, and there by moving the substrate (not shown), horizontally or orthogonally. The picker 102 may be connected to the z-picker motor system, which may include a coarse z-motor 116 and a fine z-motor 114. The fine z-motor 114 may be a vibration-inducing component (i.e. a voice coil, an ultrasonic transducer, or the like), may be a drive component that moves in approximately 1-20 μm steps, or a combination thereof to induce vibration and drive the picker tip 104 (i.e. a piezoelectric motor or the like).

Figure 2A:
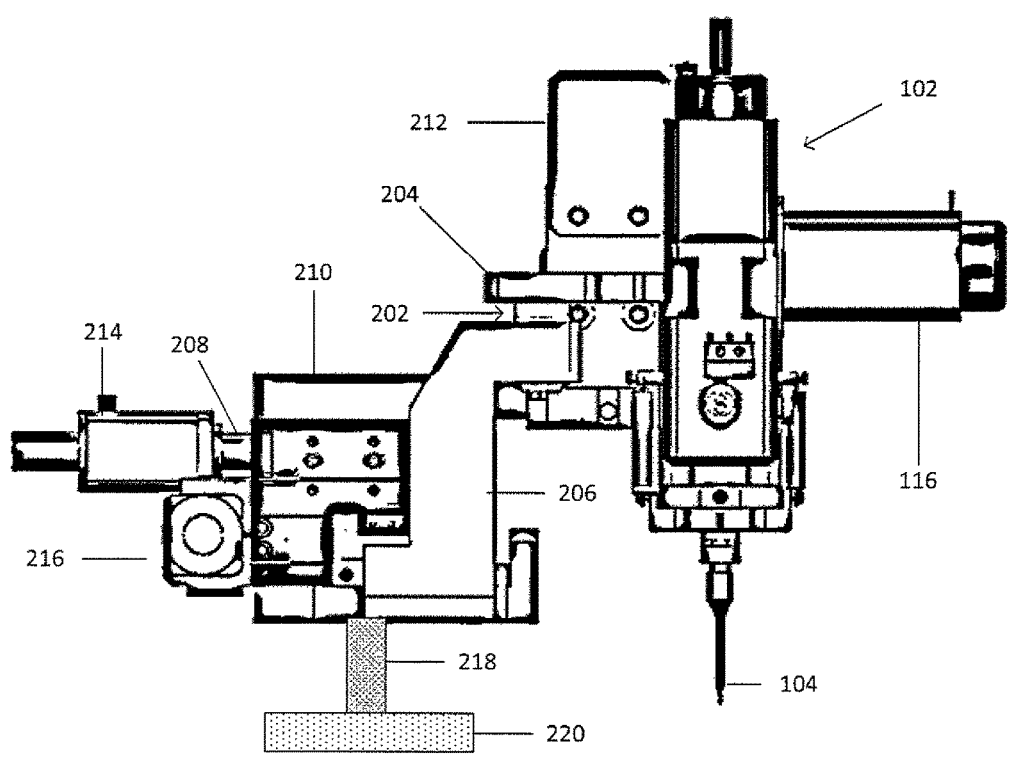
FIGS. 2A-2B show a subsystem of the scanner of FIG. 1.
Figure 2B:
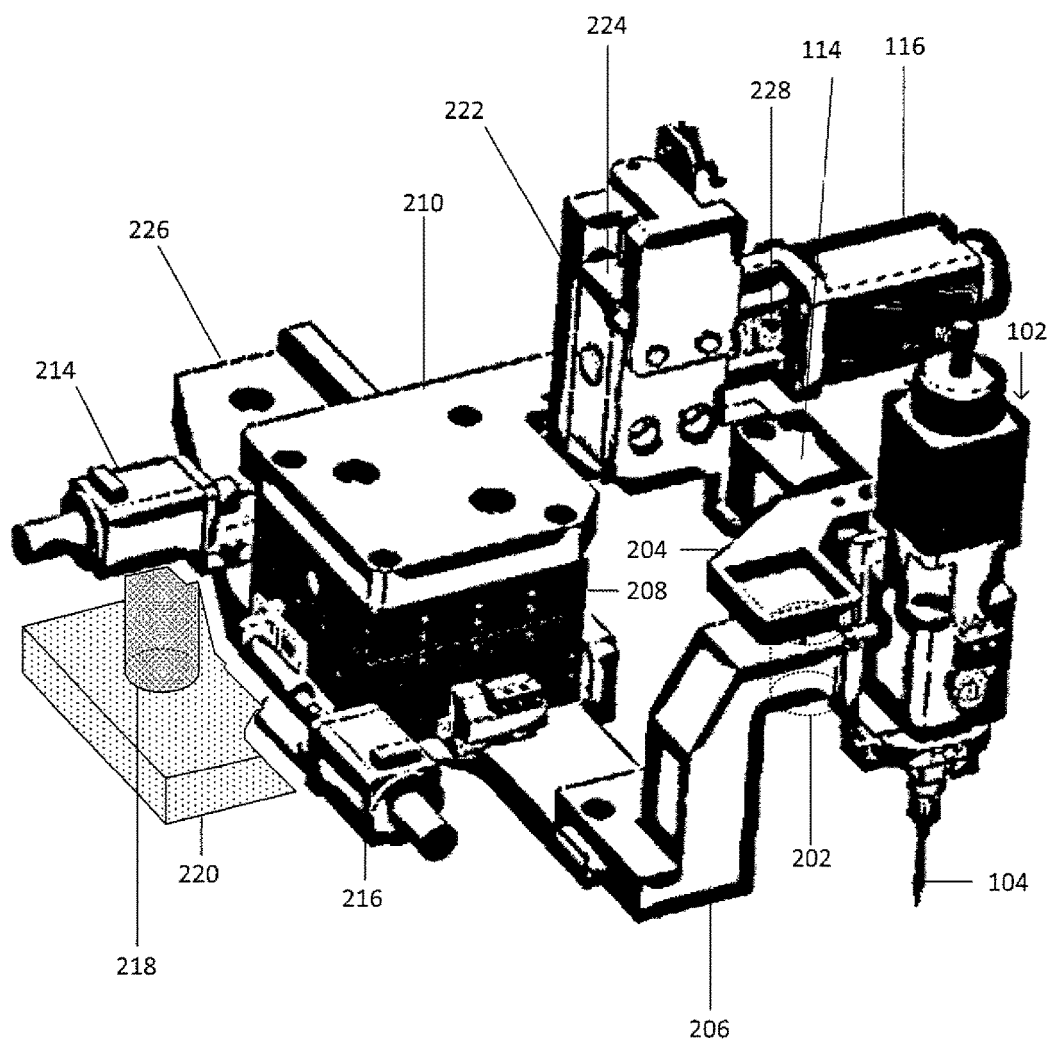

FIGS. 2A and 2B show a subsystem 200 of the picking and imaging system shown in FIG. 1. FIG. 2A shows a front view of the subsystem 200 and the FIG. 2B shows an isometric view of the subsystem 200. The subsystem 200 includes a position detector including a sensor 202 and a target plate 204. The sensor 202 may be mechanical (switch), electrical (linear encoder), capacitive, optical (laser), acoustic, inductive (linear variable differential transformer), or the like. The subsystem 200 also includes the picker 102 including the picker tip 208; and may also include the slide holder 106 to support a substrate. The slide holder 106 may be a fixed z-distance from the sensor 202 and the target plate 204 may be a fixed z-distance from the picker tip 208. The picker tip 208 and the target plate 204 may be moveable along the z-axis relative to the slide holder 106 and the sensor 202, respectively. Furthermore, the target plate 204 may be fixedly attached to the picker 102, whether directly (i.e. being mounted to a component of the picker 102) or indirectly (i.e. being mounted to a plate or bracket attached to the picker 102). The subsystem 200 may also include a reference plate 220, which may be a fixed z-distance from at least one of the sensor 202 and the slide holder 106. The subsystem 200 also includes a z-picker motor system, wherein the target plate 204 and the picker 102 are driven along the z-axis by the z-picker motor system. The z-picker motor system may include at least one of the coarse z-motor 116 and the fine z-motor 114. The fine z-motor 114 may be a piezoelectric motor. The fine z-motor 114 has a travel range of approximately 0.001-500 μm and the coarse z-motor 116 has a travel range of approximately 1-50 mm. Additionally, the z-picker motor system may include a vibration-inducing component to cause the picker 102 to oscillate along the z-axis. The vibration-inducing component may be a voice coil, an ultrasonic transducer, or a piezoelectric motor. The picker 102 may oscillate at a frequency less than or equal to approximately 10 kHz and have an amplitude of approximately 1-20 μm.

The z-picker motor system, the sensor 202, and the target plate 204 may form a closed feedback loop, whereby the position detector provides a voltage output determined by the distance between the sensor 202 and the target plate 204. The voltage output of the position detector is amplified by an amplifier and then input into a controller board which provides a second output voltage and feedback to the z-picking motor system. The z-picker motor system may then adjust the distance between the sensor 202 and the target plate 204 to a desired distance based on the second voltage output from the controller board. The distance and second output voltage relationship may have already been calibrated, such that the second output relates to a known distance whereby driving the target plate 204 towards or away from the sensor 202 and determining the second output voltage provides the desired distance. For example, when the second output voltage is 1.0 V, the target plate 204 and the sensor 202 may be 1 mm away from one another. However, when the desired distance is 2 μm, and it is known that the second voltage output is 3.1 V when the target plate 204 and the sensor 202 are 2 μm away from one another, the target plate 204 may be driven towards the sensor 202 until the second output voltage is 3.1 V.

The picker 102 may be connected to an x-y stage 208 such as by an x-y connector plate 210. The x-y stage 208 may be connected to an x-axis motor 216, a y-axis motor 214, and a base plate 226. The base plate 226 may be connected to a reference plate 220 by at least one post 218. The reference plate 220 is stationary and acts as a point or plane against which movement in the x-, y-, and z-axes may be referenced. The reference plate 220 may be mounted on vibration plates (not shown) within the scanner to inhibit the influence of vibration, whether external or internal to the picker 102, on movement and control of the picker 102. The sensor 202 may be connected to the base plate 226 by a sensor mount 206.

The coarse z-motor 116 may be connected to the picker 102 by a coupling 228. The coupling 228 may also be connected to a coarse z-stage carriage 224. A coarse z-stage base 222 may act as a guide for the coarse z-stage carriage 224 and may also include a stop 212 to limit the furthest travel of the coarse z-motor 116 relative to the slide holder 106.

Example Method I

A method for locating the substrate includes driving the picker 102 including the picker tip 104 from a holding position towards and at least partially past the slide holder 106. Alternatively, the picker 102 including the picker tip 104 may be driven from a holding position towards a substrate without touching or going past the substrate, such that the holding position is above the substrate. During the driving step, a first output is obtained by the position detector. The picker 102 including the picker tip 104 is then returned or withdrawn to the holding position. A substrate (not shown) is then inserted into the slide holder 106. The picker 102 including the picker tip 104 is then re-driven from the holding position towards the substrate until the picker tip at least touches the substrate. During the re-driving step, a second output is obtained by the position detector.

After contact, the picker 102 including the picker tip 104 overtravel until a threshold is reached. The substrate (not shown) may be located by calculating the difference between the first output and the second output, such as a point where the difference is equal to or greater than the threshold (such as 250 ADC counts) or at the point at which the first and second outputs are not equal. The first and second outputs may be plotted, stored in memory, or any appropriate manner of retaining the data for subsequent comparison, analysis, and/or use. The first and second outputs may be voltage, current, or the like.

Though the subsystem above is discussed as being driven along the z-axis, the subsystem may be driven along one of the x-, y-, or z-axes, whether based on orientation or an appropriate layout. For example, when the subsystem drives along the z-axis, the holding position may above or below the slide holder 106.

Figure 3:
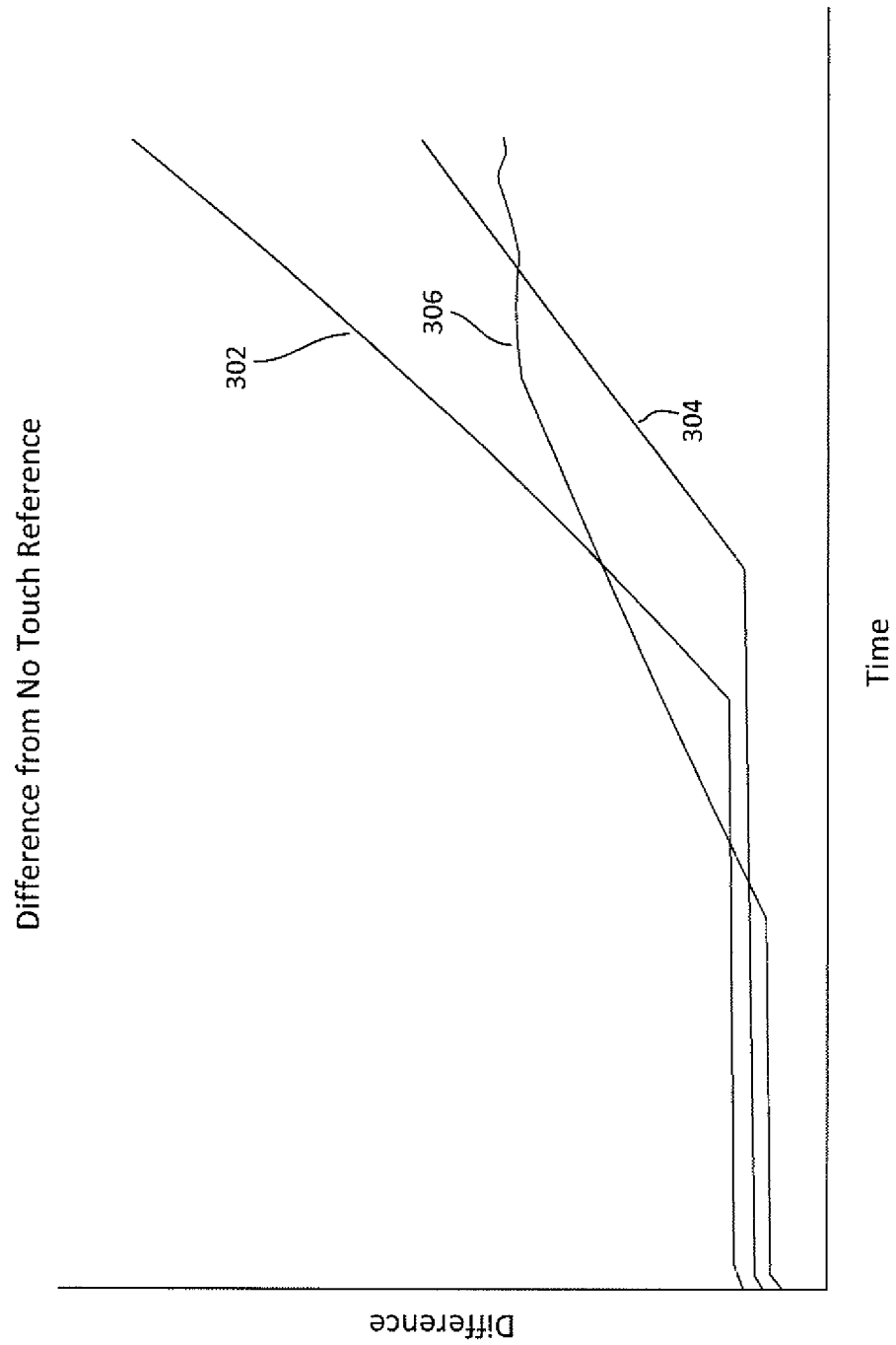
FIG. 3 shows a second output obtained at three different locations on a substrate.

FIG. 3 shows the second output obtained at three different locations on the substrate. Line 302 shows the second output when the picker 102 including the picker tip 104 touches a portion of the substrate being the stiffest, which may be the middle section. Line 304 shows the second output when the picker 102 including the picker tip 104 touches a portion of the substrate having a medium stiffness. Line 306 shows the second output when the picker 102 including the picker tip 104 touches a portion of the substrate having the least stiffness. In the example provided, the movement of the break points in the lines 302, 304, 306 may be due to the slope of the substrate.

FIG. 4A shows a first output 402 and a second output 404 superimposed. The point at which the second output 404 splits from the first output is where the substrate is touched by the picker 102 including the picker tip 104. FIG. 4B shows the difference between the first output 402 and the second output 404. In this case, the detect algorithm has been completed when the difference exceeds a threshold, such as 250 ADC counts, during overtravel. Movement and logging data are stopped as well.

Example Method II

A method for locating the substrate includes driving the picker 102 including the picker tip 104 from a holding position towards the slide holder 106. During the driving step, the picker 102 including the picker tip 104 is moved in steps, for example, from a first position to a second position. A known output is determined based on the movement of the picker 102 from the first position to the second position. The picker 102 including the picker tip 104 is then commanded to be moved from the second position to a third position. However, the picker 102 including the picker tip 104 does not travel the full distance in moving from the second position to the third position.

Figure 5A:
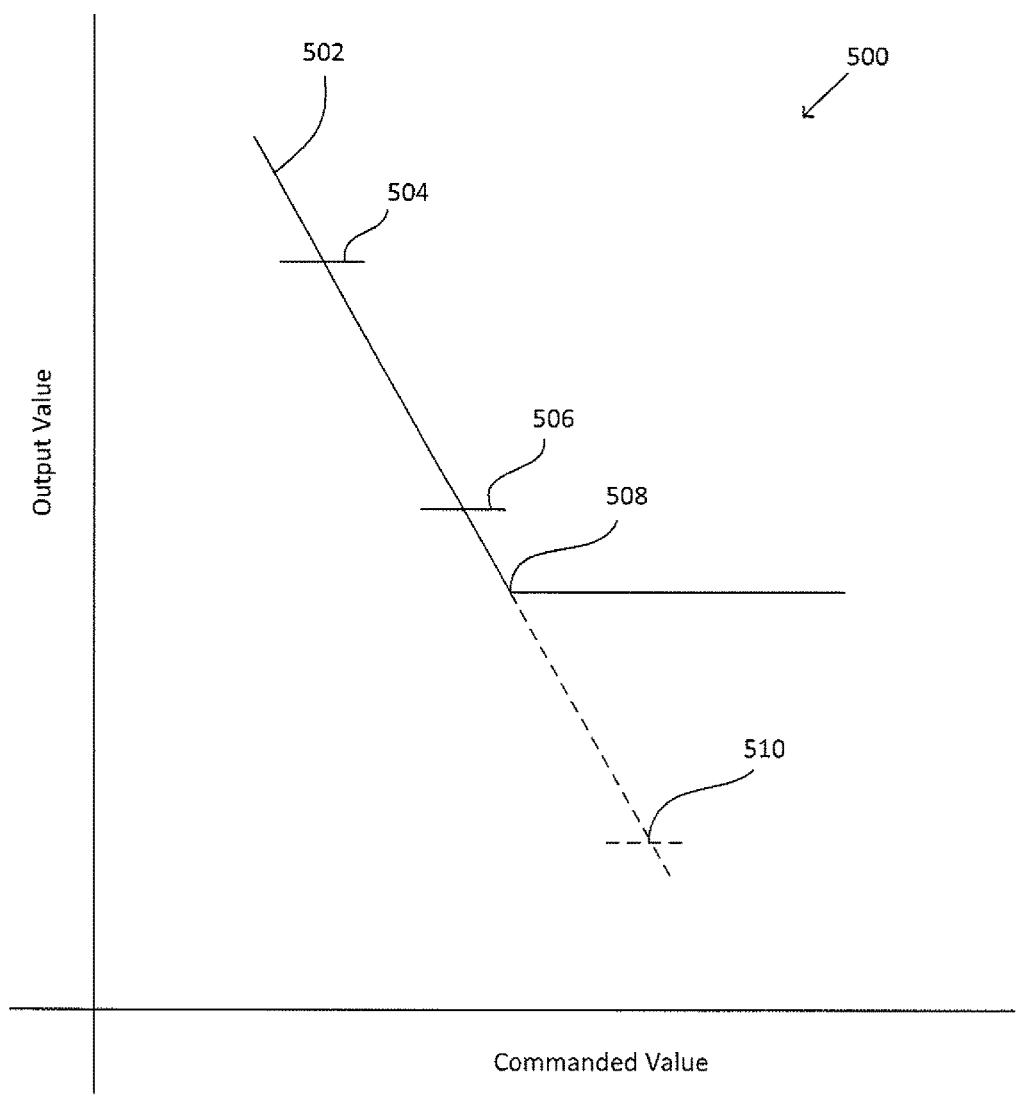
FIGS. 5A-5B show outputs.

FIG. 5A shows an actual output 502 superimposed with an expected output (the dashed line). The picker 102 including the picker tip 104 moves from a first position 504 to a second position 506. The picker 102 including the picker tip 104 is then commanded to move from the second position 506 to a third position 510. As the picker 102 is commanded to move to the third position 510, the values obtained from the position detector are expected to follow the dashed line, thereby resulting in the value of the third position 510. However, during travel, the picker 102 touches the substrate and the output therefore deviates from the expected value. After contact, the picker 102 including the picker tip 104 overtravel until a threshold is reached. The substrate (not shown) may be located by calculating the difference between the actual output and the expected output, such as a point where the difference is equal to or greater than the threshold (such as 250 ADC counts) or at the point at which the actual and expected outputs are not equal.

Example Method III

Figure 5B:
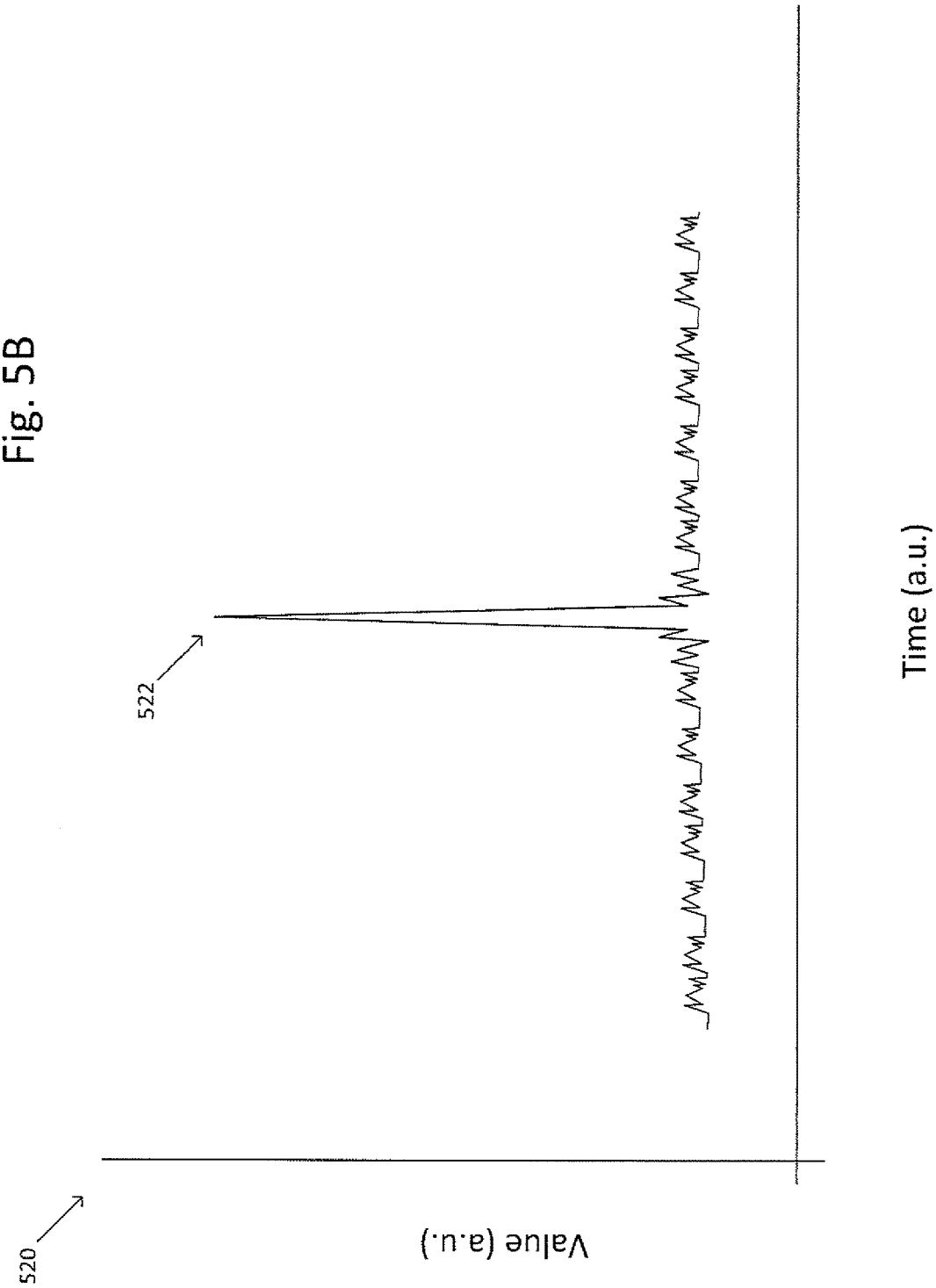

FIG. 5B shows a method 520 for locating the substrate includes driving the picker 102 including the picker tip 104 from a holding position towards and at least partially past the slide holder 106. During the driving step, mathematical computations, such second order derivatives or the like, are performed on the at least one output value obtained by the position detector to obtain a computational output. The computational output is substantially stable. Upon the picker 102 including the picker tip 104 contacting the substrate, a spike 522 is achieved during the mathematical computation of the at least one contact value. After contact, and during at least some overtravel, a computational overtravel is obtained by mathematical computation, which substantially stabilizes again, such as to the computational output during the driving step or to a value different than both the spike 522 and the computational output during the driving step.

Overtravel is the continued driving of the picker 102 including the picker tip 104 even after the picker 102 including the picker tip 104 has contacted the substrate. Overtravel may be a step performed after the at least two steps of driving and contacting. After at least contacting, overtravel may range from approximately 1 µm to approximately 1 mm, including such distances as approximately 3, 5, 7, or 10 µm.

The target analyte may be collected, and once collected, the target analyte may be analyzed using any appropriate analysis method or technique, though more specifically intracellular analysis including intracellular or extracellular protein labeling; nucleic acid analysis, including, but not limited to, protein or nucleic acid microarrays; FISH; or bDNA analysis. These techniques require isolation, permeabilization, and fixation of the target analyte prior to analysis. Some of the intracellular proteins which may be labeled include, but are not limited to, cytokeratin ("CK"), actin, Arp2/3, coronin, dystrophin, FtsZ, myosin, spectrin, tubulin, collagen, cathepsin D, ALDH, PBGD, Akt1, Akt2, c-myc, caspases, survivin, p27$^{kip}$, FOXC2, BRAF, Phospho-Akt1 and 2, Phospho-Erk1/2, Erk1/2, P38 MAPK, Vimentin, ER, PgR, PI3K, pFAK, KRAS, ALKH1, Twist1, Snail1, ZEB1, Slug, Ki-67, M30, MAGEA3, phosphorylated receptor kinases, modified histones, chromatin-associated proteins, and MAGE. In order to fix, permeabilize, or label, fixing agents (such as formaldehyde, formalin, methanol, acetone, paraformaldehyde, or glutaraldehyde), detergents (such as saponin, polyoxyethylene, digitonin, octyl β-glucoside, octyl β-thioglucoside, 1-S-octyl-β-D-thioglucopyranoside, polysorbate-20, CHAPS, CHAPSO, (1,1,3,3-Tetramethyl-butyl)phenyl-polyethylene glycol or octylphenol ethylene oxide), or labeling agents (such as fluorescently-labeled antibodies, Pap stain, Giemsa stain, or hematoxylin and eosin stain) may be used.

It should be understood that the method and system described and discussed herein may be used with any appropriate suspension or biological sample, such as blood, bone marrow, cystic fluid, ascites fluid, stool, semen, cerebrospinal fluid, nipple aspirate fluid, saliva, amniotic fluid, vaginal secretions, mucus membrane secretions, aqueous humor, vitreous humor, vomit, and any other physiological fluid or semi-solid. It should also be understood that a target analyte can be a cell, such as ova or a circulating tumor cell ("CTC"), a fetal cell (i.e. a trophoblast, a nucleated red blood cell, a fetal white blood cell, a fetal red blood cell, etc.), a circulating endothelial cell, an immune cell (i.e. naïve or memory B cells or naïve or memory T cells), a vesicle, a liposome, a protein, a nucleic acid, a biological molecule, a naturally occurring or artificially prepared microscopic unit having an enclosed membrane, a parasite, a microorganism, or an inflammatory cell.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments are presented by way of examples for purposes of illustration and description. They are not intended to be exhaustive of or to limit this disclosure to the precise forms described. Many modifications and variations are possible in view of the above teachings. The embodiments are shown and described in order to best explain the principles of this disclosure and practical applications, to thereby enable others skilled in the art to best utilize this disclosure and various embodiments with various modifications as are suited to the particular use contemplated. It is intended that the scope of this disclosure be defined by the following claims and their equivalents.

We claim:

1. A method comprising:
    providing a system comprising
        a picker comprising a picker tip,
        a slide holder comprising a substrate comprising a target analyte, and
        a position detector comprising
            a sensor fixed at a set distance in at least one axis relative to the slide holder, and
            a target plate fixed at a set distance in at least one axis relative to the picker tip;
    driving the picker towards the substrate and the target plate towards the sensor;
    contacting the substrate with the picker tip; and
    overtraveling the substrate with the picker tip.

2. The method of claim 1, wherein the sensor is fixed the set distance along the z-axis relative to the slide holder, and wherein the target plate is fixed the set distance along the z-axis relative to the picker tip.

3. The method of claim 1, wherein the driving, contact, and overtraveling steps are performed along the z-axis.

4. The method of claim 1, further comprising locating the substrate along the first axis by determining a position along the first axis at which one of the following occurs:
    (i) a current or voltage output obtained by the position detector during the overtraveling step is not equal to a current or voltage output obtained by the position detector during the driving step,
    (ii) a difference between a current or voltage output obtained by the position detector during the driving step and a current or voltage output obtained by the position detector during the overtraveling step is greater than or equal to a pre-determined threshold,
    (iii) a less-than-expected current or voltage output is obtained by the position detector when the picker is instructed to travel from a second position to a third position, wherein the picker contacts the substrate thereby not moving the full distance between the second and third positions, wherein an expected value is obtained when the picker moves from a first position to the second position during the driving step, and wherein the first and second positions are equal in distance to the second and third positions, or
    (iv) a deviation from current or voltage outputs obtained by the position detector during the driving step and the overtraveling step, wherein the deviation is a current or voltage output obtained by the position detector during the contacting step.

5. The method of claim 4, further comprising isolating the target analyte from the substrate with the picker.

6. The method of claim 1, the system further comprising a piezoelectric motor to perform at least one of the driving, contacting, and overtraveling steps with the picker along the z-axis.

7. The method of claim 1, the system further comprising a deflection detector on a side of the substrate opposite the picker tip.

8. The method of claim 1, the system further comprising at least one motor to perform at least one of the driving, contacting, and overtraveling steps with the picker along at least one axis.

9. The method of claim 1, further comprising isolating the target analyte from the substrate with the picker.

10. The method of claim 9, wherein the target analyte is a cell, an ova, a circulating tumor cell, a fetal cell, a trophoblast, a nucleated red blood cell, a fetal white blood cell, a fetal red blood cell, a circulating endothelial cell, an immune cell, a naïve B cell, a memory B cell, a naïve T cell, a memory T cell, a liposome, a protein, a nucleic acid, a biological molecule, a naturally occurring microscopic unit having an enclosed membrane, an artificially prepared microscopic unit having an enclosed membrane, a parasite, a microorganism, or an inflammatory cell.

11. The method of claim 1, wherein the target analyte is a cell, an ova, a circulating tumor cell, a fetal cell, a trophoblast, a nucleated red blood cell, a fetal white blood cell, a fetal red blood cell, a circulating endothelial cell, an immune cell, a naïve B cell, a memory B cell, a naïve T cell, a memory T cell, a liposome, a protein, a nucleic acid, a biological molecule, a naturally occurring microscopic unit having an enclosed membrane, an artificially prepared microscopic unit having an enclosed membrane, a parasite, a microorganism, or an inflammatory cell.

12. The method of claim 1, wherein the sensor is inductive, mechanical, capacitive, optical, or acoustic.

13. The method of claim 1, wherein the sensor is an encoder.

14. The method of claim 1, further comprising withdrawing the picker a set amount after the contacting step.

* * * * *